United States Patent
Chuang et al.

(10) Patent No.: US 8,002,966 B2
(45) Date of Patent: Aug. 23, 2011

(54) BIOSENSOR, BIOSTRIP, AND MANUFACTURE METHOD OF DETERMINATION OF URIC ACID BY A NON-ENZYMATIC REAGENT

(75) Inventors: Ya-Hsin Chuang, Taipei (TW); Hsin-Yi Lin, Taipei (TW); An-Ye Wei, Taipei (TW); Che-Ming Wang, Taipei (TW)

(73) Assignee: Health & Life Co., Ltd., Taipei (TW)

( * ) Notice: Subject to any disclaimer, the term of this patent is extended or adjusted under 35 U.S.C. 154(b) by 1019 days.

(21) Appl. No.: 11/782,517

(22) Filed: Jul. 24, 2007

(65) Prior Publication Data

US 2008/0121523 A1 May 29, 2008

(30) Foreign Application Priority Data

Nov. 24, 2006 (TW) ................. 95143555 A

(51) Int. Cl.
*G01N 27/327* (2006.01)
(52) U.S. Cl. ............. 205/787; 205/792; 204/403.01
(58) Field of Classification Search .......... 204/400, 204/416, 403.01–403.15; 205/775, 792, 205/787, 789, 780.5
See application file for complete search history.

(56) References Cited

U.S. PATENT DOCUMENTS 5,639,672 A * 6/1997 Burd et al. .............. 436/525
6,054,039 A * 4/2000 Shieh ..................... 205/778

FOREIGN PATENT DOCUMENTS

JP       02-251766 A   * 10/1990

OTHER PUBLICATIONS

JPO abstract of JP 02-251766 A Takahashi et al., patent published on Oct. 9, 1990).*
English language translation of Takahashi JP 02-251766, Mar. 1, 2011.*

* cited by examiner

*Primary Examiner* — Alex Noguerola
(74) *Attorney, Agent, or Firm* — WPAT, P.C.; Anthony King

(57) ABSTRACT

The present invention discloses a biosensor, a biostrip and a manufacture method of determination of uric acid by a non-enzymatic reagent, and particularly to the applications of determination of uric acid by a non-enzymatic reagent, which is useful for the quantification of the uric acid levels in the samples. The biosensor of the invention comprises at least a sensor, a biostrip and a non-enzymatic reagent for the determination of uric acid, wherein the biostrip has at least two working electrodes and at least one reaction zone and the non-enzymatic reagent for the determination of uric acid is disposed in the reaction zone on the biostrip, and has at least a tetrazolium salt and an active electron mediator, wherein the reaction zone is used for a sample to initiate the oxidation-reduction reaction of the tetrazolium salt and then, according to the oxidation-reduction reaction, with the active electron mediator and the two working electrodes, an electronic signal is transmitted to the sensor to produce a corresponding microcurrent intensity which is in turn calculated by the sensor to reflect the uric acid level in the sample.

35 Claims, 3 Drawing Sheets

BIOSENSOR, BIOSTRIP, AND MANUFACTURE METHOD OF DETERMINATION OF URIC ACID BY A NON-ENZYMATIC REAGENT

This application claims foreign priority from Taiwanese application no. 095143555, filed on Nov. 24, 2006.

BACKGROUND OF THE INVENTION

1. Field of the Invention

The present invention is directed to a biosensor, a biostrip and a manufacture method of determination of uric acid by a non-enzymatic reagent, and particularly to the applications of determination of uric acid by a non-enzymatic reagent.

2. Description of the Prior Art

Modern people's lives are intense and busy. Irregular schedules, abnormal diet and insufficient rest and exercise lead to many diseased conditions. For example, many people are susceptible to gout due to over-tiredness, stress, over-eating and alcohol intake. In view of the causes of gout, hyperuricemia is also one of the essential biological bases of gout, and usually refers to a uric acid level of over 7 mg/dl. In addition, it is indicated in many reports and publications that a high uric acid content from 5% to 12% can lead to gout. The clinical manifestations of gout can be categorized into asymptomatic hyperuricemia, acute gouty arthritis, intermittent periods, gouty tophus, chronic arthritis, renal lesion and etc. The attack of gout is rapid and is often without any preceding symptoms. However, when the pain occurs, it is like being cut by a knife, having a luxation or being doused with icy water. In addition, obvious reddish swelling and feverish pain can often be experienced at the joints and the peripheral tissues thereof. It is also reported that among 60% to 70% of patients, the first attack often occurs at the joint of the big toe. In addition to pharmacological management, current treatment of gout and hyperuricemia generally includes the advice to avoid a high purine diet or food rich in purine such as animal guts, sardines, oysters, clams, crabs and the like. The high uric acid level is controlled by the adoption of a low purine diet. However, research has shown that even with such a strict diet control, the uric acid level can only be limitedly lowered to 1-2 mg/dl. Nevertheless, a strict diet control is still necessary, because gout is usually accompanied by the occurrence of hyperlipidemic, hyperglycemic or hypertensive diseases.

Most of the currently available biosensors for uric acid in the market work through the interaction between uricase and uric acid to produce an oxidation-reduction reaction and then transmit the resulting micro-current to the biosensor by an electronic transducer. The most common disadvantage of such a system is that uricase is susceptible to the interference from the oxygen level in the blood as well as to the interference from the ionic content in the blood and therefore a measurement error can often result. Moreover, the uricase available in the current market is still a high-price material.

In view of the various problems in the prior art systems, the inventors of the present invention have proposed a biosensor, biostrip and manufacture method of determination of uric acid by a non-enzymatic reagent based on years of practical experiences in developing biosensors, biostrips and manufacture methods thereof as a solution to improve the above-mentioned disadvantages.

SUMMARY OF THE INVENTION

In view of the above, the object of the invention is to provide a biosensor which uses a non-enzymatic uric acid reagent instead of the conventional uricase and therefore overcomes the measurement disadvantage as well as the high cost of uricase. In other words, the invention provides a non-enzymatic biosensor for uric acid, which works through the reaction of uric acid with tetrazolium salts. Since uric acid can produce an eneaminol structure under basic conditions, such a reduction structure can react with tetrazolium salts and then the electronic exchange of the reaction can be transmitted by an electronic mediator so that the object of measurement can be achieved.

The measuring process of the invention is susceptible neither to the interference from the oxygen level in the blood nor to the interference from the ionic content in the blood.

Various tetrazolium salts are currently available in the market. Since a wide selection is available, the application thereof is much more flexible. Therefore, the invention uses tetrazolium salts to obtain the required detection.

The biosensor with a non-enzymatic uric acid reagent of the invention comprises a sensor, a biostrip and a determination of uric acid by a non-enzymatic reagent, wherein the biostrip has at least two working electrodes and at least one reaction zone and the determination of uric acid by a non-enzymatic reagent disposed in the reaction zone on the biostrip that has at least a tetrazolium salt and an active electron mediator. It is to be noted that the biostrip of the invention can use a human body fluid as the sample, such as whole blood (including microcapillary blood and venous blood), plasma, serum or urine, to initiate the oxidation-reduction reaction of the tetrazolium salt in the reaction zone on the biostrip. Then, according to the oxidation-reduction reaction, with the active electron mediator and the two working electrodes on the biostrip, an electronic signal is transmitted to the sensor to produce a corresponding micro-current intensity which is in turn calculated by the sensor to reflect the uric acid level in the sample.

In addition, the above non-enzymatic uric acid reagent further comprises an excipient buffer solution to dissolve the tetrazolium salt and the active electron mediator therein. The excipient buffer solution is made of a mixture of at least one buffer salt such as sodium carbonate, sodium hydrogen carbonate and the like in appropriate ratios with at least one water-soluble excipient such as hydroxypropyl methyl cellulose and the like.

According to the above-mentioned biosensor with a non-enzymatic uric acid reagent, the invention further provides a manufacture method for biostrip with a non-enzymatic uric acid reagent, which comprises at least the following steps:

(a) disposing two working electrodes on a biostrip, (b) dissolving at least one buffer salt such as sodium carbonate, sodium hydrogen carbonate and the like and at least one water-soluble excipient such as hydroxypropyl methyl cellulose and the like in pure water to form an excipient buffer solution, (c) dissolving a tetrazolium salt and an active electron mediator such as phenazine ethosulfate and the like in the excipient buffer solution to form a non-enzymatic uric acid reagent, (d) filtrating the non-enzymatic uric acid reagent through a filter membrane such as cellulose acetate membrane and the like with a pore size of between 0.22 μm and 10 μm and then dispensing and spreading the non-enzymatic uric acid reagent in the reaction zone on the biostrip, and (e) drying the biostrip.

The technical characteristics of the invention and the effects achieved thereby are further illustrated with the following detailed description in conjunction with the preferred embodiments.

DETAILED DESCRIPTION OF THE INVENTION

The biosensor, biostrip and manufacture method of determination of uric acid by a non-enzymatic reagent according to the preferred embodiments of the invention will be described in the following section with reference to the relevant drawings.

Figure 1:
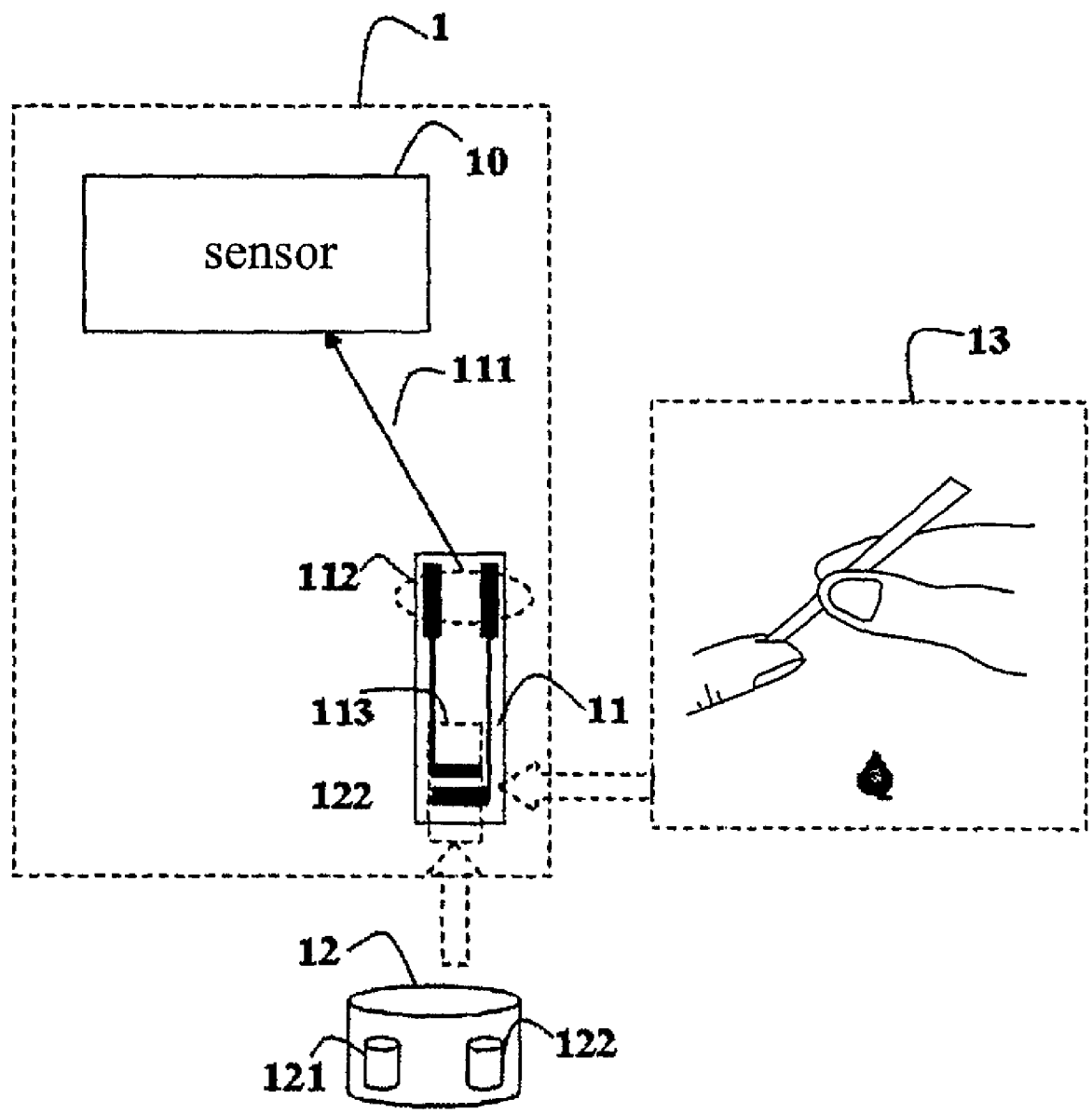
FIG. 1 is a block diagram of the biosensor with a non-enzymatic uric acid reagent of the invention.

With reference to FIG. 1, which is a block diagram of the biosensor with a non-enzymatic uric acid reagent of the invention, the biosensor 1 of the invention is comprised of at least a sensor 10, a biostrip 11 and a non-enzymatic reagent 12 for the determination of uric acid. The sensor 10 receives the electronic signal 111 from the biostrip 11. Therefore, the biostrip 11 has at least two working electrodes 112 and at least one reaction zone 113. In the subject example, the a non-enzymatic reagent 12 is disposed in the reaction zone 113, which consists essentially of two major parts of the excipient buffer solution 121 and the tetrazolium salt/active electron mediator 122. The working electric potential of the biostrip 11 of the subject example is preferably 0.01-0.6 V. A human body fluid (or the "sample") 13 such as whole blood (including microcapillary blood and venous blood), plasma, serum, urine and the like is provided to initiate the oxidation-reduction reaction of the tetrazolium salt 122. Then, the active electron mediator 122 can transmit the electronic signal 111 of the oxidation-reduction reaction to the sensor 10 by the working electrodes 112 to produce a corresponding micro-current intensity which is in turn calculated by the sensor to reflect the uric acid level in the sample 13. In the subject example, the preferred testing time is 1-30 sec and the applicable uric acid level is preferably 1-30 mg/dL.

The excipient buffer solution generally includes carbonate buffer solution, Kolthoff buffer solution, borate buffer solution or equivalent buffer solutions thereof and is used to provide a basic condition of pH 8.5-12.3. The excipient buffer solution comprises at least one buffer salt and at least one water-soluble excipient. The buffer salt generally includes sodium carbonate, sodium hydrogen carbonate, lithium carbonate, lithium hydrogen carbonate, boric acid, borax or any of the combinations thereof or equivalent salts. The buffer salt is preferably present in a weight to volume ratio (w/v) of 0.05%-2%. The water-soluble excipient generally includes cellulose and derivatives thereof, synthetic high molecular polymers, water-soluble high molecular polymers, water-soluble high molecular polymer salts or any of the combinations thereof or equivalent high molecular polymer excipients. Cellulose and derivatives thereof preferably include methyl cellulose (MC), carboxy methyl cellulose (CMC), hydroxypropyl methyl cellulose (HPMC), hydroxypropyl cellulose (HPC), hydroxy ethyl cellulose (HEC) or any of the combinations thereof or equivalent cellulose excipients. Synthetic water-soluble high molecular polymers preferably include polyvinylpyrrolidone (PVP), polymethacrylamide (PMA), polyacrylamide (PAM), polyallylamine (PAA) or any of the combinations thereof or equivalent water-soluble high molecular polymer excipients. Natural water-soluble high molecular polymer excipient such as alginate or equivalent excipients thereof can also be used. The water-soluble excipient can present in a weight to volume ratio (w/v) of 0.01%-8.0%. The tetrazolium salt includes preferably neotetrazolium chloride (NT), tetranitroblue tetrazolium chloride (TNBT), blue tetrazolium chloride (BT), iodonitrotetrazolium chloride, nitroblue tetrazolium chloride (NBT), thiazolyl blue tetrazolium bromide salt (MTT salt), nitro blue monotetrazolium chloride, tetrazolium violet, 2,3,5-triphenyl-2-H-tetrazolium chloride, thiocarbamyl nitro blue tetrazolium chloride (TCNBT), tetrazolium XTT, 2-2'-benzothiazolyl-5-styryl-3-(4'-phthalhydrazidyl)tetrazolium chloride (BSPT), distyryl nitroblue tetrazolium chloride (DSNBT) or any of the combinations thereof or equivalent tetrazolium salts. Generally, the tetrazolium salt can be present in a weight to volume ratio (w/v) of 0.1%-10%. The active electron mediator preferably includes potassium ferricyanide, para-benzoquinone, quinone, quinone chlorimide, quinone imide, phenazine methosulfate (PMS), phenazine ethosulfate (PES) or any of the combinations thereof or equivalent active electron mediators. Generally, the active electron mediator can be present in a weight to volume ratio (w/v) of 0.02%-5.0%.

Figure 2:
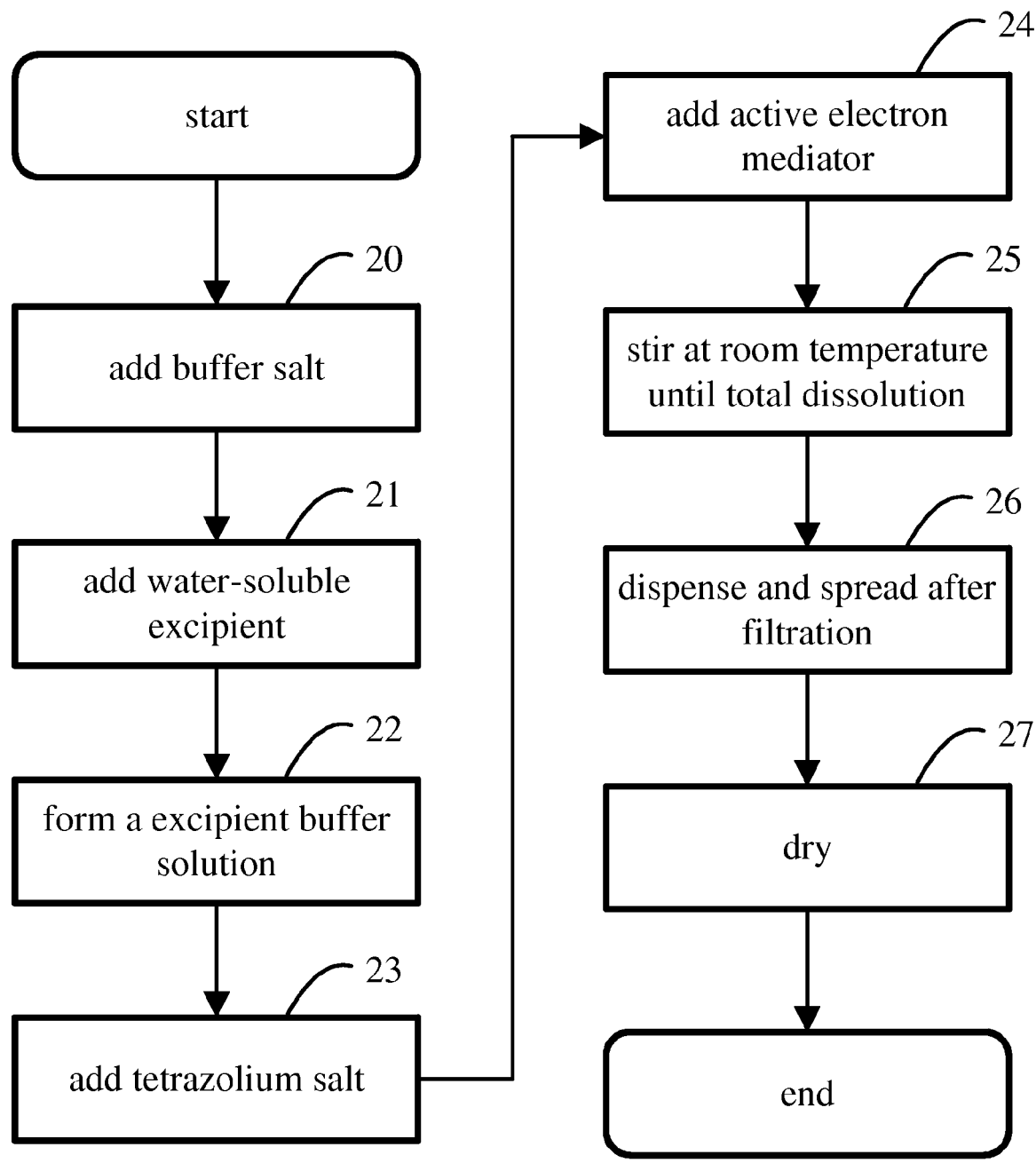
FIG. 2 is a schematic diagram of the manufacture method of the biostrip with a non-enzymatic uric acid reagent of the invention.

With reference to FIG. 2, which is a schematic diagram of the manufacture method of the biostrip with a non-enzymatic uric acid reagent of the invention, the subject process comprises at least the following steps:

Step 20: dissolving the buffer salt, for example, from 10 to 30 g sodium carbonate or from 0.1 to 0.3 g sodium hydrogen carbonate in 30-80 ml pure water;

Step 21: dissolving the water-soluble excipient, for example, from 100 to 200 mg hydroxypropyl methyl cellulose in said pure water;

Step 22: stirring said pure water at room temperature until total dissolution and adjusting the pH of the solution to be within the range of 8.5-12.3 to form an excipient buffer solution;

Step 23: dissolving the tetrazolium salt, for example, from 6 to 10 mg tetrazolium salt in said excipient buffer solution;

Step 24: dissolving the active electron mediator, for example, from 15 to 20 mg phenazine ethosulfate in said excipient buffer solution;

Step 25: stirring said excipient buffer solution at room temperature until total dissolution;

Step 26: filtrating the above reagent through a filter membrane, for example, a cellulose acetate membrane with a pore size of 1.0 μm, and then dispensing and spreading it in the reaction zone on the biostrip, and Step 27: drying the above biostrip at a temperature of 40° C. to 65° C.

The biostrip also has two working electrodes. The electrodes can transmit the electronic signal of the oxidation-reduction reaction to produce a micro-current intensity which can then be calculated to reflect the uric acid level of the samples. A human body fluid (or the "sample") such as whole blood (including microcapillary blood and venous blood), plasma, serum, urine and the like is provided. In the subject example, the preferred testing time is 1-30 sec and the applicable uric acid level is preferably 1-30 mg/dL. Moreover, the filter membrane is, for example, a high molecular polymer membrane such as a cellulose acetate membrane, with a preferable pore size of 0.22 μm-10 μm. The excipient buffer solution generally includes carbonate buffer solution, Kolthoff buffer solution, borate buffer solution or equivalent buffer solutions thereof and is used to provide a basic condition of pH 8.5-12.3. The excipient buffer solution comprises at least one buffer salt and at least one water-soluble excipient. The buffer salt generally includes sodium carbonate, sodium hydrogen carbonate, lithium carbonate, lithium hydrogen carbonate, boric acid, borax or any of the combinations thereof or equivalent salts. The buffer salt is preferably present in a weight to volume ratio (w/v) of 0.05%-2%. The water-soluble excipient generally includes cellulose and derivatives thereof, synthetic high molecular polymers, water-soluble high molecular polymers, water-soluble high molecular polymer salts or any of the combinations thereof or equivalent high molecular polymer excipients. Cellulose and derivatives thereof preferably include methyl cellulose (MC), carboxy methyl cellulose (CMC), hydroxypropyl methyl cellulose (HPMC), hydroxypropyl cellulose (HPC), hydroxy ethyl cellulose (HEC) or any of the combinations thereof or equivalent cellulose excipients. Synthetic water-soluble high molecular polymer preferably includes polyvinylpyrrolidone (PVP), polymethacrylamide (PMA), polyacrylamide (PAM), polyallylamine (PAA) or any of the combinations thereof or equivalent water-soluble high molecular polymer excipients. Natural water-soluble high molecular polymer excipient such as alginate or equivalent excipients thereof can also be used. The water-soluble excipient can be present in a weight to volume ratio (w/v) of 0.01%-8.0%. The tetrazolium salt preferably includes neotetrazolium chloride (NT), tetranitroblue tetrazolium chloride (TNBT), blue tetrazolium chloride (BT), iodonitrotetrazolium chloride, nitroblue tetrazolium chloride (NBT), thiazolyl blue tetrazolium bromide salt (MTT salt), nitro blue monotetrazolium chloride, tetrazolium violet, 2,3,5-triphenyl-2-H-tetrazolium chloride, thiocarbamyl nitro blue tetrazolium chloride (TCNBT), tetrazolium XTT, 2-2'-benzothiazolyl-5-styryl-3-(4'-phthalhydrazidyl)tetrazolium chloride (BSPT), distyryl nitroblue tetrazolium chloride (DSNBT) or any of the combinations thereof or equivalent tetrazolium salts. Generally, the tetrazolium salt can be present in a weight to volume ratio (w/v) of 0.1%-10%. The active electron mediator preferably includes potassium ferricyanide, parabenzoquinone, quinone, quinone chlorimide, quinone imide, phenazine methosulfate (PMS), phenazine ethosulfate (PES) or any of the combinations thereof or equivalent active electron mediators. Generally, the active electron mediator can be present in a weight to volume ratio (w/v) of 0.02%-5.0%.

Figure 3:
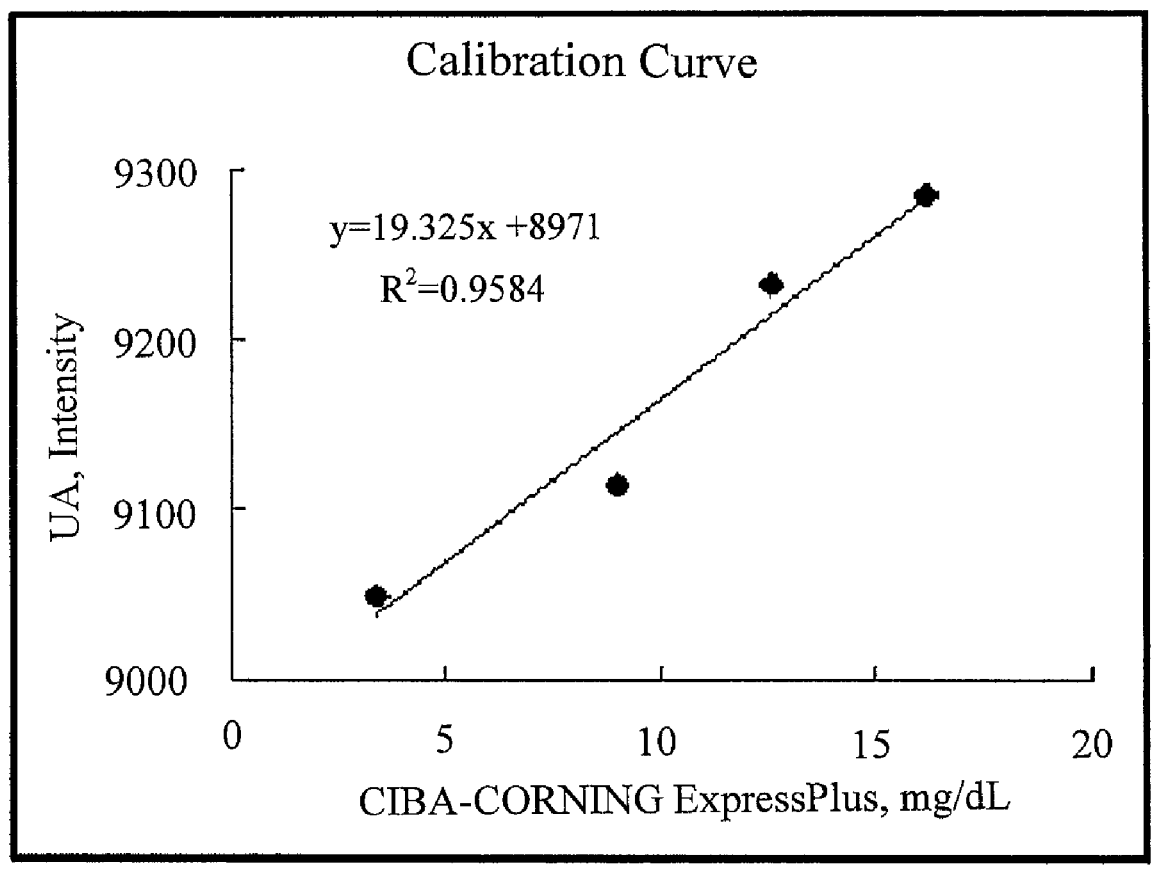
FIG. 3 is a diagram showing different uric acid levels with the corresponding current intensity detected by the sensor.

FIG. 3 is a diagram showing the current intensity detected at the sensor from venous whole blood with the addition of uric acid in different ratios. The working electric potential is set at 100 mV. The blood samples are centrifuged to obtain plasma. Concentration analysis is performed thereto with CIBA-Corning ExpressPlus and the calibration curve is obtained by plotting the plasma concentration against the uric acid reaction intensity. The curve thus obtained corresponds to Y=19.235X+8971, with a correlation coefficient ($R^2$) of 0.9584.

The above description is provided for illustration only. It can be in no way construed as a limitation to the present invention. Any modifications or changes without departing from the spirit of the invention, including but not limited to any combination of the elements described in the embodiments of the invention by software, hardware or firmware, are intended to be within the scope of the invention as defined by the appending claims.

BRIEF DESCRIPTION OF THE ELEMENT NUMERALS

1: biosensor
10: sensor
11: biostrip
111: electronic signal
112: working electrode
113: reaction zone
112: non-enzymatic reagent
121: excipient buffer solution
122: tetrazolium salt/active electron mediator
13: human body fluid or sample
20-27: process steps

What is claimed is:

1. A biosensor with a non-enzymatic uric acid reagent, which at least comprises:
   a sensor, which receives an electronic signal;
   a biostrip, which has at least two working electrodes and at least one reaction zone; and
   a non-enzymatic reagent for the determination of uric acid, which is disposed in the reaction zone and has at least a tetrazolium salt and an active electron mediator;
   wherein the reaction zone is used for a sample to initiate the oxidation-reduction reaction of the tetrazolium salt and then, according to the oxidation-reduction reaction, with the active electron mediator and the two working electrodes, an electronic signal is transmitted, which is in turn calculated to reflect the uric acid level in the sample.

2. The biosensor with the non-enzymatic uric acid reagent of claim 1, wherein the non-enzymatic uric acid reagent further comprises an excipient buffer solution and the excipient buffer solution comprises at least one buffer salt and at least one water-soluble excipient.

3. The biosensor with the non-enzymatic uric acid reagent of claim 2, wherein the excipient buffer solution includes carbonate buffer solution, Kolthoff buffer solution or borate buffer solution.

4. The biosensor with the non-enzymatic uric acid reagent of claim 2, wherein the water-soluble excipient includes cellulose and derivatives thereof, synthetic water-soluble high molecular polymers, water-soluble high molecular polymer salts or any of the combinations thereof.

5. The biosensor with the non-enzymatic uric acid reagent of claim 1, wherein the active electron mediator includes potassium ferricyanide, parabenzoquinone, quinone, quinone chlorimide, quinone imide, phenazine methosulfate (PMS), phenazine ethosulfate (PES) or any of the combinations thereof.

6. The biosensor with the non-enzymatic uric acid reagent of claim 1, wherein the electronic signal produces a corresponding micro-current intensity by the sensor to reflect the uric acid level in the sample.

7. A method for detecting an uric acid level by using a biosensor with a non-enzymatic uric acid reagent of claim 1, comprising providing a sample to the reaction zone to initiate the oxidation-reduction reaction of the tetrazolium salt, transmitting an electronic signal of the oxidation-reduction reaction to the sensor by the active electron mediator and the working electrodes, and calculating the electronic signal to reflect the uric acid level in the sample.

8. The method of claim 7, wherein a working electric potential difference of the two working electrodes is within the range between 0.01 V and 0.6 V.

9. The method of claim 7, wherein a testing time at the reaction zone is in the range of between 1 and 30 seconds.

10. A biostrip with a non-enzymatic uric acid reagent, comprising:
    at least two working electrodes
    at least one reaction zone; and
    a non-enzymatic reagent for the determination of uric acid, which is disposed in the reaction zone and has at least a tetrazolium salt and an active electron mediator;
    wherein the reaction zone is used for a sample to initiate the oxidation-reduction reaction of the tetrazolium salt and then, according to the oxidation-reduction reaction, with the active electron mediator and the two working electrodes, an electronic signal is transmitted, which is in turn calculated to reflect the uric acid level in the sample.

11. The biostrip with the non-enzymatic uric acid reagent of claim 10, wherein the non-enzymatic uric acid reagent further comprises an excipient buffer solution and the excipient buffer solution comprises at least one buffer salt and at least one water-soluble excipient.

12. The biostrip with the non-enzymatic uric acid reagent of claim 11, wherein the water-soluble excipient includes cellulose and derivatives thereof, synthetic water-soluble high molecular polymers, water-soluble high molecular polymer salts or any of the combinations thereof.

13. The biostrip with the non-enzymatic uric acid reagent of claim 10, wherein the excipient buffer solution includes carbonate buffer solution, Kolthoff buffer solution or borate buffer solution.

14. The biostrip with the non-enzymatic uric acid reagent of claim 10, wherein the active electron mediator includes potassium ferricyanide, parabenzoquinone, quinone, quinone chlorimide, quinone imide, phenazine methosulfate (PMS), phenazine ethosulfate (PES) or any of the combinations thereof.

15. The biostrip with the non-enzymatic uric acid reagent of claim 10, wherein the electronic signal corresponds to a micro-current intensity to reflect the uric acid level in the sample.

16. A method for detecting an uric acid level by using a biostrip with a non-enzymatic uric acid reagent of claim 10, comprising providing a sample to the reaction zone to initiate the oxidation-reduction reaction of the tetrazolium salt, transmitting an electronic signal of the oxidation-reduction reaction to the biosensor by the active electron mediator and the working electrodes, and calculating the electronic signal to reflect the uric acid level in the sample.

17. The method of claim 16 wherein a working electric potential difference of the two working electrodes is within the range between 0.01 V and 0.6 V.

18. The method of claim 16 wherein a testing time at the reaction zone is in the range of between 1 and 30 seconds.

19. A manufacture method of a biostrip with a non-enzymatic uric acid reagent, which comprises:
disposing two working electrodes on a biostrip, and
dispensing and spreading a non-enzymatic uric acid reagent in the reaction zone on the biostrip;
wherein the non-enzymatic uric acid reagent comprises at least an excipient buffer solution, a tetrazolium salt and an active electron mediator.

20. The manufacture method of a biostrip with the non-enzymatic uric acid reagent of claim 19, wherein the excipient buffer solution includes carbonate buffer solution, Kolthoff buffer solution or borate buffer solution.

21. The manufacture method of a biostrip with the non-enzymatic uric acid reagent of claim 19, wherein the excipient buffer solution comprises at least one buffer salt and at least one water-soluble excipient.

22. The manufacture method of a biostrip with the non-enzymatic uric acid reagent of claim 21, wherein the water-soluble excipient includes cellulose and derivatives thereof, synthetic water-soluble high molecular polymers, water-soluble high molecular polymer salts or any of the combinations thereof.

23. The manufacture method of a biostrip with the non-enzymatic uric acid reagent of claim 19, wherein the active electron mediator includes potassium ferricyanide, parabenzoquinone, quinone, quinone chlorimide, quinone imide, phenazine methosulfate (PMS), phenazine ethosulfate (PES) or any of the combinations thereof.

24. A manufacture method of a biostrip with a non-enzymatic uric acid reagent, which comprises:
dissolving at least one buffer salt and at least one water-soluble excipient in pure water to form an excipient buffer solution,
dissolving a tetrazolium salt and an active electron mediator in the excipient buffer solution to form a non-enzymatic uric acid reagent;
filtrating the non-enzymatic uric acid reagent through a filter membrane and then dispensing and spreading the non-enzymatic uric acid reagent in the reaction zone on a biostrip.

25. The manufacture method of a biostrip with the non-enzymatic uric acid reagent of claim 24, wherein the excipient buffer solution includes carbonate buffer solution, Kolthoff buffer solution or borate buffer solution.

26. The manufacture method of a biostrip with the non-enzymatic uric acid reagent of claim 24, wherein the water-soluble excipient includes cellulose and derivatives thereof, synthetic water-soluble high molecular polymers, water-soluble high molecular polymer salts or any of the combinations thereof.

27. The manufacture method of a biostrip with the non-enzymatic uric acid reagent of claim 24, wherein the active electron mediator includes potassium ferricyanide, parabenzoquinone, quinone, quinone chlorimide, quinone imide, phenazine methosulfate (PMS) or phenazine ethosulfate (PES).

28. The manufacture method of a biostrip with the non-enzymatic uric acid reagent of claim 24, wherein the pore size of the filter membrane is from 0.22 µm to 10 µm.

29. The manufacture method of a biostrip with the non-enzymatic uric acid reagent of claim 24, which further comprises disposing two working electrodes on the biostrip.

30. The manufacture method of a biostrip with the non-enzymatic uric acid reagent of claim 24, which further comprises drying the biostrip.

31. A non-enzymatic uric acid reagent, comprising:
a tetrazolium salt; and
an active electron mediator;
wherein the tetrazolium salt is used for a sample to initiate the oxidation-reduction reaction and then, according to the oxidation-reduction reaction, an electronic exchange is performed with the active electron mediator and an electronic signal resulting from the electronic exchange is transmitted, which is in turn calculated to reflect the uric acid level in the sample.

32. The non-enzymatic uric acid reagent of claim 31, wherein the non-enzymatic uric acid reagent further comprises an excipient buffer solution and the excipient buffer solution comprises at least one buffer salt and at least one water-soluble excipient.

33. The non-enzymatic uric acid reagent of claim 32, wherein the excipient buffer solution includes carbonate buffer solution, Kolthoff buffer solution or borate buffer solution.

34. The non-enzymatic uric acid reagent of claim 32, wherein the water-soluble excipient includes cellulose and derivatives thereof, synthetic water-soluble high molecular polymers, water-soluble high molecular polymer salts or any of the combinations thereof.

35. The non-enzymatic uric acid reagent of claim 31, wherein the active electron mediator includes potassium ferricyanide, parabenzoquinone, quinone, quinone chlorimide, quinone imide, phenazine methosulfate (PMS), phenazine ethosulfate (PES) or any of the combinations thereof.

* * * * *